(12) United States Patent
Matsumoto et al.

(10) Patent No.: US 8,668,871 B2
(45) Date of Patent: Mar. 11, 2014

(54) SENSING DEVICE AND BIOSENSOR

(75) Inventors: Akira Matsumoto, Tokyo (JP); Yuji Miyahara, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 0 days.

(21) Appl. No.: 13/513,939

(22) PCT Filed: Jul. 20, 2011

(86) PCT No.: PCT/JP2011/066393
§ 371 (c)(1),
(2), (4) Date: Jun. 5, 2012

(87) PCT Pub. No.: WO2012/011479
PCT Pub. Date: Jan. 26, 2012

(65) Prior Publication Data
US 2012/0244037 A1 Sep. 27, 2012

(30) Foreign Application Priority Data

Jul. 22, 2010 (JP) ................. 2010-164955

(51) Int. Cl.
*G01N 33/53* (2006.01)
(52) U.S. Cl.
USPC ............. 422/69; 422/400; 422/420; 422/425; 562/7

(58) Field of Classification Search
USPC ................ 422/400, 40, 420, 425, 690; 562/7
See application file for complete search history.

(56) References Cited

U.S. PATENT DOCUMENTS

2012/0283403 A1* 11/2012 Matsumoto et al. .......... 526/239

FOREIGN PATENT DOCUMENTS

| JP | 05-018931 A | 1/1993 |
| JP | 2005517164 A | 6/2005 |
| JP | 2010-107496 A | 5/2010 |

* cited by examiner

*Primary Examiner* — Monique Cole
(74) *Attorney, Agent, or Firm* — Fox Rothschild LLP; Robert J. Sacco

(57) ABSTRACT

Provided are a sensing device and a biosensor that are capable of achieving stable performance in sensing saccharides or hydroxyl group-containing polymers, and that can be stored for a long time. The biosensor 8 of the present invention uses, as a component for sensing glucose, a sensing device 16 in which a completely synthetic phenylboronic acid compound 21 is bound without using enzymes that have been conventionally used. Consequently, the biosensor 8 can eliminate the problem of protein denaturation to achieve stable performance in sensing glucose, and it is possible to achieve the biosensor 8 can be stored for a long time.

11 Claims, 6 Drawing Sheets

SENSING DEVICE AND BIOSENSOR

CROSS REFERENCE TO RELATED APPLICATIONS

The application is the National Phase application of International Application Serial No. PCT/JP2011/066393, filed Jul. 20, 2011, which claims priority under The Paris Convention to Japanese Patent Application No. 2010-164955 filed on Jul. 22, 2010, which are incorporated herein in their entireties.

DESCRIPTION

1. Technical Field

The present invention relates to a sensing device and a biosensor.

2. Background Art

Recently, as glucose sensors for use in blood glucose measurement, glucose sensors using glucose oxidase (GOD), glucose dehydrogenase (GDH), hexokinase (HX), peroxidase (POD), materials of combination thereof, and the like, have been known (for example, refer to Patent Document 1).

Such glucose sensors are configured to be able to determine the glucose concentration by colorimetry for a concentration change in substances that are produced or disappear upon enzymatic reaction between these reagent components and glucose or by detection of a change in oxidation-reduction potential.

PRIOR ART DOCUMENT

Patent Document

Patent Document 1: Japanese Patent Unexamined Application Publication No. H5-18931 A

DISCLOSURE OF THE INVENTION

Problems to be Solved by the Invention

However, these methods using enzymatic reaction have problems in that the performance of sensing saccharides becomes unstable due to protein denaturation, and in most cases long-term storage is difficult because of a problem of the dependence on dissolved enzymes thereof.

Then, the present invention was made in light of the above matters. An object of the present invention is to provide a sensing device and a biosensor that are capable of achieving stable performance in sensing saccharides or hydroxyl group-containing polymers and that can be stored for a long time.

Means for Solving the Problems

To solve such problems, a first aspect of the present invention is characterized in that a phenylboronic acid compound represented by the following Formula (3):

[Formula 3]

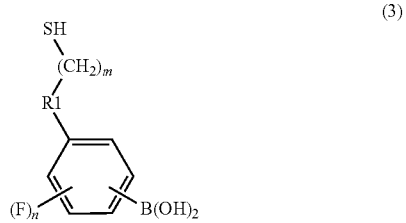

(where m is an integer equal to or greater than 1; F is independently present; n is any one of 1, 2, 3 and 4; and R1 represents a divalent linking group) is chemisorbed to a substrate surface by a thiol group at the end.

Further, a second aspect of the present invention is that the above Formula (3) is specifically represented by the Formula (4):

[Formula 4]

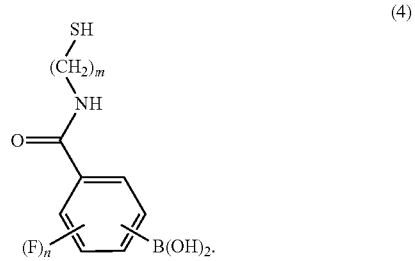

Moreover, a third aspect of the present invention is characterized in that the m is equal to or greater than 8.

In addition, a fourth aspect of the present invention is characterized in that the sensing device according to any one of claims 1 to 3 is provided at a sensing medium, and the sensing medium detects a change in any one or more of the following physical characteristics including an optical characteristic, an oscillation characteristic and an electrical characteristic, which occur due to a bond of a saccharide or hydroxyl group-containing polymer to the phenylboronic acid compound.

Further, a fifth aspect of the present invention is characterized in that the sensing medium is a field effect transistor, and the sensing device is provided on a gate insulating film of the field effect transistor.

Moreover, a sixth aspect of the present invention is characterized in that the sensing device is disposed apart from the gate insulating film, and a gate-insulating-film-side metal layer provided on the gate insulating film is electrically connected to the sensing device via wiring.

In addition, a seventh aspect of the present invention is characterized in that the sensing medium is an optical waveguide member in which the sensing device is provided at the external surface; and an optical characteristic changes at a boundary portion between the optical waveguide member and the sensing device when the saccharide or hydroxyl group-containing polymer binds to the phenylboronic acid compound.

Further, an eighth aspect of the present invention is characterized in that the sensing medium is a piezoelectric member in which the sensing device is provided at the external surface; and an oscillation characteristic changes at a boundary portion between the piezoelectric member and the sensing device when the saccharide or hydroxyl group-containing polymer binds to the phenylboronic acid compound.

Effect of the Invention

Since the sensing device of the first aspect and the biosensor of the fourth of the present invention use a completely synthetic phenylboronic acid compound free from protein as a material for sensing saccharides and hydroxyl group-containing polymers without using enzymes that have been conventionally used, it is possible to eliminate the problem of protein denaturation to achieve stable performance in sensing saccharides or hydroxyl group-containing polymers, and achieve a biosensor that can be stored for a long time.

Figure 1:
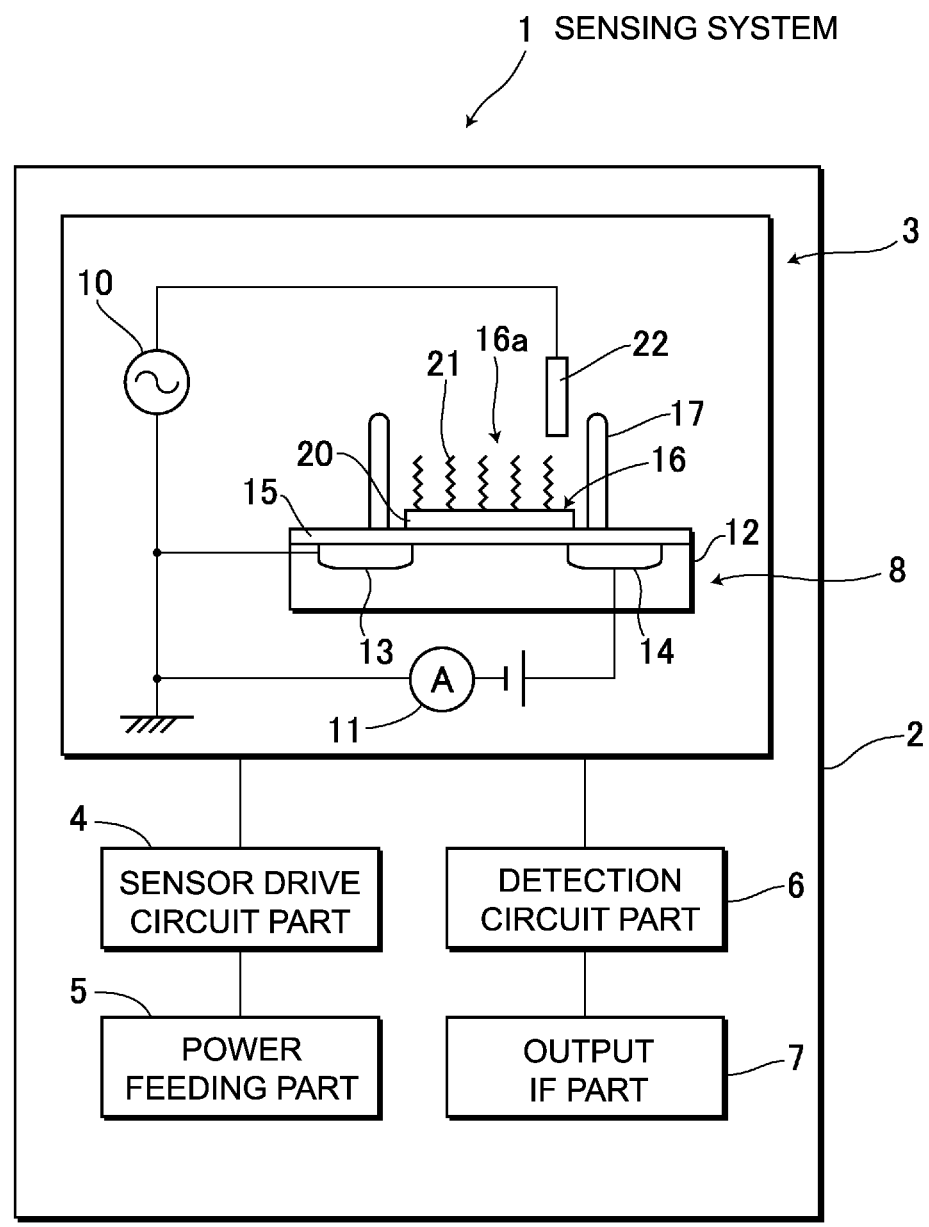
FIG. 1 is a schematic diagram that shows the overall configuration of the sensing system according to the first embodiment.

DESCRIPTION OF REFERENCE NUMERALS 8, 32, 41, 51 Biosensor
16 Sensing device
21 Phenylboronic acid compound
42 Solid-phase substrate (sensing medium)
53 Quartz crystal oscillator (sensing medium)

EMBODIMENTS OF THE INVENTION

The following describes the embodiments of the present invention in detail based on the drawings.

(1) First Embodiment (1-1) Configuration of Sensing System

In FIG. 1, 1 indicates a sensing system as a whole, and the sensing system 1 has a configuration in which a biosensor part 3, a sensor drive circuit part 4 that provides a signal to and drives the biosensor part 3, a power feeding part 5 that supplies a power source to each circuit part, a detection circuit part 6 that processes an output from the biosensor part 3 and outputs a detection signal, and an output interface (output IF) part 7 for outputting a detection signal to the outside are integrally formed in one body on a printed mounting board 2.

The biosensor part 3 includes a biosensor 8, which is a detection medium, with a field effect transistor (hereinafter also referred to as FET) structure. The biosensor part 3 can be driven by electric power fed from a power source 10 based on a control signal of the sensor drive circuit part 4 mounted on the printed mounting board 2. Actually, the biosensor part 3 can perform sampling of a change in current output from the biosensor 8 with an ammeter 11, and send the detection result to the detection circuit part 6. Accordingly, in the sensing system 1, the detection result from the biosensor 8 can be processed by the detection circuit part 6, and extracted as a predetermined detection signal from the output IF part 7.

Here, the biosensor 8 includes a source 13 and a drain 14 formed at the surface of a semiconductor substrate 12, and a gate insulating film 15 formed on the semiconductor substrate 12, the source 13 and the drain 14, and has a structure in which a sensing device 16 is provided at the surface of the gate insulating film 15. Actually, at the gate insulating film 15, a sensing region of the sensing device 16 that is surrounded by a measurement cell wall 17 is formed, so that a glucose sample solution such as a blood sample can be retained within the sensing region partitioned by the measurement cell wall 17.

In addition to this structure, the sensing device 16 has a structure in which one surface of a metal layer 20 made of, for example, an Au evaporated thin film is coated with a phenylboronic acid compound 21 (mentioned below), and is configured in such a manner that the metal layer 20 is formed as a gate on the gate insulating film 15, and the phenylboronic acid compound 21 can be exposed as a sensing surface 16a in the sensing region.

In such as the biosensor 8, since the metal layer 20 is applied with voltage by using a reference electrode 22, for example, and in this situation a glucose sample solution is poured into the sensing region to immerse the reference electrode 22 and the sensing surface 16a in the glucose sample solution, a current flows between the source 13 and the drain 14.

Then, in the biosensor 8, when glucose covalently binds to the phenylboronic acid compound 21 at the sensing surface 16a in the glucose sample solution, a negative charge is generated. In response to this, the voltage applied to the metal layer 20 changes, and the current that flows between the source 13 and the drain 14 also changes. This enables the biosensor 8 to perform sampling of this current change with the ammeter 11 and detect the glucose in the glucose sample solution based on the current change.

Additionally, in this embodiment, it is possible to integrate the entire structure including the biosensor part 3 on the single printed mounting board 2, thereby enabling detection of glucose with a very small and simple structure. Further, the biosensor 8 is a noninvasive and unlabeled measurement method for detecting the intrinsic charge of the molecules provided on the sensing surface 16a by synchronization with a change in transistor characteristics, and is also capable of real-time measurement. Moreover, the biosensor 8 can be manufactured with lower costs and a smaller size as optical equipments such as a laser are not required, and can be easily made highly dense and massively parallel by semiconductor processing techniques. Thus, the biosensor 8 potentially covers the main requirements that are demanded in high throughput formulation.

Figure 2:
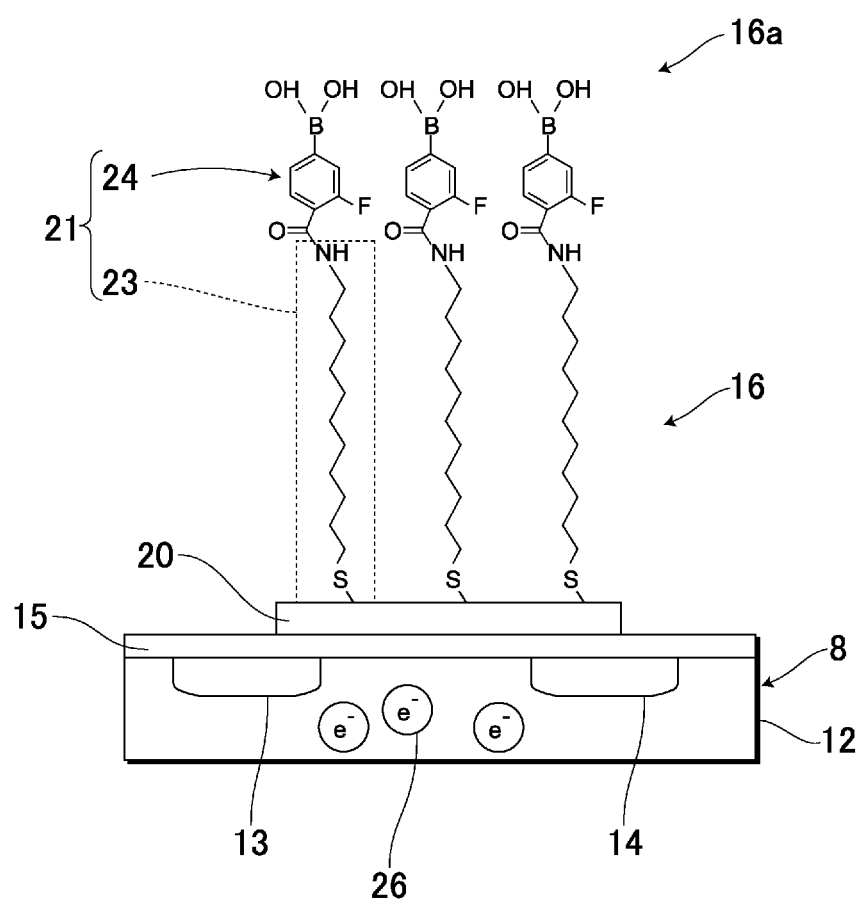
FIG. 2 is a schematic diagram that serves to explain a sensing surface in a biosensor.

Here, the phenylboronic acid compound 21 that coats the metal layer 20 consists of a Self-Assembled Monolayer (SAM) 23 one end of which is chemisorbed to the substrate surface of the metal layer 20, and a fluorinated phenylboronic acid group 24 bound to the other end of the self-assembled monolayer 23, as shown in FIG. 2. The fluorinated phenylboronic acid group 24 can be disposed as the sensing surface 16a on the metal layer 20. In the case of this embodiment, the phenylboronic acid compound 21 is represented by the following Formula (5):

[Formula 5]

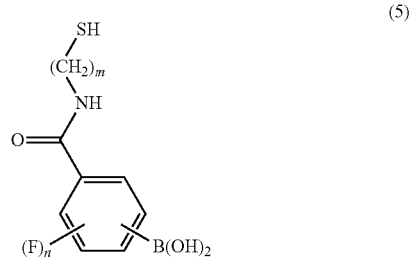

(5)

(where m is an integer equal to or greater than 1; F is independently present; and n is any one of 1, 2, 3 and 4).

Here, the fluorinated phenylboronic acid group has a structure in which fluorines are substituted for one or more hydrogens (that is, equal to or greater than one and equal to or less than four hydrogens) on the phenyl ring of the phenylboronic acid group, and the carbon of the carbonyl group is bound to the phenyl ring. Such the fluorinated phenylboronic acid group is highly hydrophilic. Further, since the phenyl ring is fluorinated, the value of pKa can be controlled to equal to or lower than 7.4 which is the level of a living body. Therefore, the fluorinated phenylboronic acid group can acquire the capability of saccharide recognition in the body environment.

It should be noted that, in the phenylboronic acid compound represented by the above Formula (5), when n is 1 so that one hydrogen on the phenyl ring is substituted by fluorine, F and B(OH)$_2$ may be introduced at any of the ortho, meta and para positions.

Here, in the case of this embodiment, the self-assembled monolayer 23 has an alkanethiol molecule, which is a long chain molecule in which a thiol group (—SH) is added to an end of a hydrocarbon chain, so that the thiol group (—SH) at one end can be chemisorbed to the substrate surface of the metal layer 20. Further, the self-assembled monolayer 23 has a structure in which the carbon of the carbonyl group of the fluorinated phenylboronic acid group 24 is bound to the amino terminal by condensation reaction or the like, so that the fluorinated phenylboronic acid group 24 can be disposed at the external surface of the metal layer 20.

It should be noted that m in the above Formula (5) is preferably about—8-30, and when m is equal to or greater than 8, it is easy to form on the metal layer 20 the self-assembled monolayer 23, which consists of a long chain molecule in which a thiol group (—SH) is added to an end of a hydrocarbon chain. Additionally, FIG. 2 shows the phenylboronic acid compound 21 in the case of m=11 and n=1.

The phenylboronic acid compound 21 thus disposed at the substrate surface of the metal layer 20 can generate a negative charge by a binding of glucose to the boronic acid. The negative charge generated by the binding between the boronic acid of the phenylboronic acid compound 21 and glucose depends on the concentration of glucose in the glucose sample solution, and can generate a negative charge 26 as a physical change in a channel region between the source 13 and the drain 14.

Thus, the biosensor 8 catches the ratio of anionization of the phenylboronic acid compound 21, which depends on the concentration of glucose in the glucose sample solution, as a current signal that flows between the source 13 and the drain 14, to thereby able to determine the concentration of glucose in the glucose sample solution based on a change of the current signal.

(1-2) Method of Manufacturing Sensing Device

Figure 3:
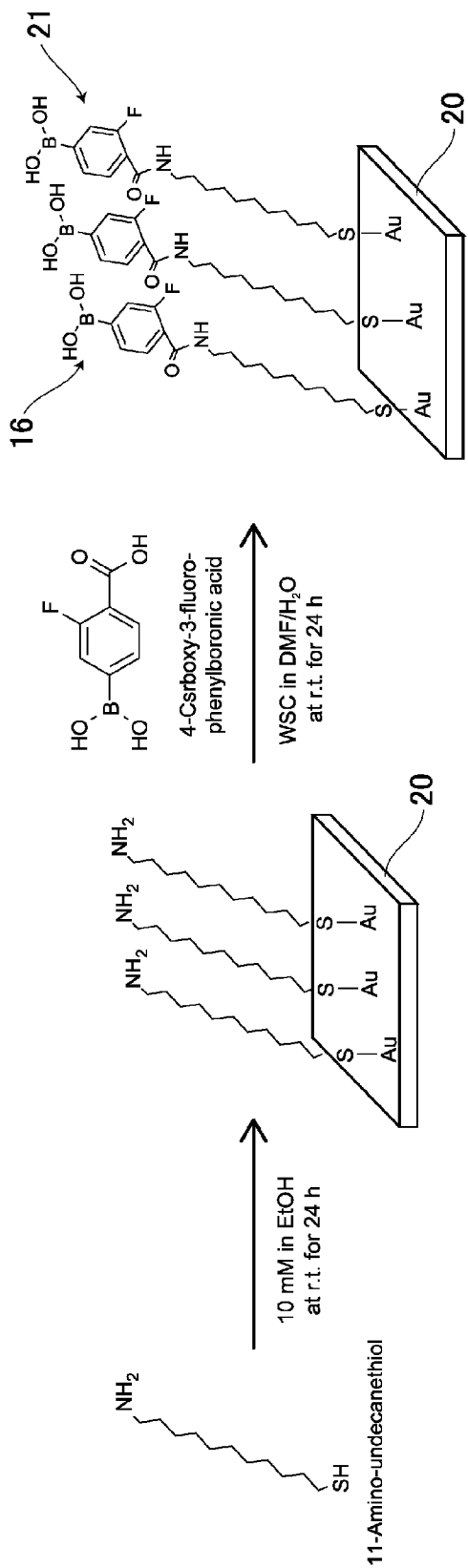
FIG. 3 is a schematic diagram that shows a method of manufacturing the sensing device according to the present invention.

Next, such as the sensing device 16 as shown in FIG. 2 can be formed by the steps set forth below. In this case, the metal layer 20 made of an Au evaporated thin film is formed by gold sputtering, and at the substrate surface of the metal layer 20, the self-assembled monolayer 23, which is an organic molecule, is formed by chemisorption. Specifically, after plasma cleaning of the metal layer 20, 11-amino-undecanethiol is dissolved in an ethanol solution (EtOH) as shown in FIG. 3, to prepare a mixed solution with 10 mM of the 11-amino-undecanethiol, followed by immersing the metal layer 20 in this mixed solution at a room temperature (r.t) for about 24 hours. Accordingly, the thiol group of the 11-amino-undecanethiol can be chemisorbed to gold, so that the self-assembled monolayer 23 can be formed at the metal layer 20.

Subsequently, after 4-carboxy-3-fluorophenylboronic acid is dissolved in DMF (N,N-dimethylformamide)/H$_2$O to prepare a solution of 10 mM 4-carboxy-3-fluorophenylboronic acid, five mole equivalents of WSC (1-ethyl-3-(3-dimethylaminopropyl)carbodiimide hydrochloride) are added to this solution, to thereby activate the carboxyl group.

Then, the metal layer 20 modified with the self-assembled monolayer is immersed in this solution at a room temperature for 24 hours and is introduced with fluorinated phenylboronic acid group. Thus, the metal layer 20 to which the phenylboronic acid compound 21 is chemisorbed can be prepared.

In this way, in the biosensor 8, it is possible to form the sensing surface 16a in which the phenylboronic acid compound 21 to be bound to glucose is arranged in the vicinity of the metal layer 20 which functions as a gate. This enables it to accurately and easily detect a change in the negative charge 26 at the sensing surface 16a due to the binding between the phenylboronic acid compound 21 and glucose.

Additionally, the above description of the embodiment stated the case of manufacturing a sensing device in which the phenylboronic acid compound 21 is disposed at the substrate surface by, first of all, binding an alkanethiol molecule, which is a long chain molecule, to the substrate surface of the metal layer 20 to prepare the self-assembled monolayer, and then binding the fluorinated phenylboronic acid group 24 to the end of this self-assembled monolayer. However, the present invention is not limited to this, and may be configured to manufacture a sensing device in which the phenylboronic acid compound 21 is disposed at the substrate surface by binding an alkanethiol molecule, which is a long chain molecule, to the fluorinated phenylboronic acid group 24 to prepare the phenylboronic acid compound 21, and then binding the thiol group at the end of this phenylboronic acid compound 21 to the substrate surface of the metal layer 20.

(1-3) Regarding Phenylboronic Acid Compound

Next, regarding the phenylboronic acid compound 21, other embodiments are described as follows. Not only the phenylboronic acid compound 21 represented by the above-mentioned Formula (5) but also the phenylboronic acid compound 21 represented by the following Formula (6) can be used for the sensing device 16 according to the present invention:

[Formula 6]

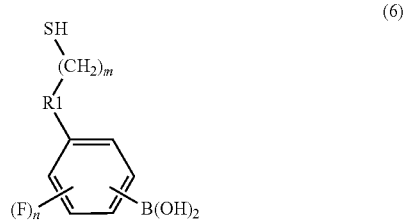

(where m is an integer equal to or greater than 1; F is independently present; n is any one of 1, 2, 3 and 4; and R1 represents a divalent linking group).

The divalent linking group represented by R1 includes a linking group containing at least one, two or more bonds selected from the group consisting of carbamoyl bond, amino bond, alkyl bond, ether bond, ester bond, thioester bond, thioether bond, sulfonamide bond, urethane bond, sulfonyl bond, imine bond, urea bond, thiourea bond, and the like.

As above, the phenylboronic acid compound has a structure in which a single or a plurality of fluorines are substituted for hydrogen on the phenyl ring of the phenylboronic acid group, and the thiol group (—SH) is bound to the phenyl ring via m hydrocarbons and the linking group R1.

Even such as the phenylboronic acid compound is highly hydrophilic, further, since the phenyl ring is fluorinated, the value of pKa can be controlled to equal to or lower than 7.4 which is the level of a living body. Therefore, the phenylboronic acid compound can acquire the capability of saccharide recognition in the body environment.

(1-4) Operations and Effects

In the above-described structure, as represented by the above Formula (6), the biosensor 8 is configured to use the sensing device 16 in which the phenylboronic acid compound is chemisorbed to the substrate surface of the metal layer 20, the phenylboronic acid compound being formed by binding the fluorinated phenylboronic acid group, in which the hydrogen on the phenyl ring of the phenylboronic acid group is substituted by a single or a plurality of fluorines, to the end of the self-assembled monolayer 23.

This enables the biosensor 8 to determine the glucose concentration of a blood sample or the like by measuring a current change between the source 13 and the drain 14 that occurs due to generation of a negative charge that is generated at the sensing surface 16$a$ because glucose binds to the phenylboronic acid compound.

In addition, since the biosensor 8 uses as a material for sensing glucose the sensing device 16 in which a completely synthetic phenylboronic acid compound free from protein is chemisorbed to the metal layer 20 without using enzymes conventionally used, it is possible to eliminate the concern of protein denaturation to achieve stable performance in sensing glucose, and achieve the biosensor 8 that can be stored for a long time.

Further, in the biosensor 8, since the phenyl ring of the phenylboronic acid compound is fluorinated, pKa can be set equal to or lower than 7.4, which is the level of a living body. As a result, the biosensor 8 can also be used under neutral pH condition such as a blood sample, and thus can be applied to measurement of blood glucose level.

It should be noted that the present invention is not limited to the present embodiment and can be embodied with various modifications within the scope of the outline of the present invention. For example, although the above description of the embodiment stated the case where the sensing target is glucose as a saccharide to be sensed, the present invention is not limited to this, and the sensing target may be any other saccharide that has a 1,2-diol or 1,3-diol structure, such as galactose, mannose or fructose, or a hydroxyl group-containing polymer, such as polyvinyl alcohol.

Moreover, the above-described first embodiment can employ various FETs used for conventional biosensors, Complementary Metal Oxide Semiconductor (CMOS) devices, or the like, and can employ both of n-MOS and p-MOS. These FETs can be applied with sensing media having various structures as long as each sensing medium includes a source that supplies carriers (free electrons or holes), a drain at which the carriers supplied from this source arrive, and a gate for controlling a flow of carriers between the source and the drain.

Further, the metal layer 20 formed on the gate insulating film 15 may be made of a material, such as Ag, for example, as long as the thiol group at the end of the phenylboronic acid compound can be chemisorbed to the material, but is preferably made of the material of Au.

EXAMPLES (1-5) Relationship Between Glucose Concentration and Potential Change

Next, a field effect transistor having the sensing device shown in FIG. 3 on the gate insulating film 15 was manufactured, and the periphery of the sensing device was partitioned by a measurement cell wall, to manufacture a biosensor in which a sample solution could be retained within the partitioned sensing region. Then, to the sample solution that was retained within the sensing region, glucose was continuously added, to examine how the potential in this field effect transistor would change while the glucose concentration was being changed. As a result, the measurement result x1 as shown in FIG. 4 could be obtained.

Here, as the sample solution, phosphate buffered saline (PBS), which was adjusted to pH 7.4 and with 155 mM NaCl the same osmotic pressure as that in a living body, was prepared. To this phosphate-buffered saline, glucose was continuously added, to thereby gradually increase the glucose concentration.

Figure 4:
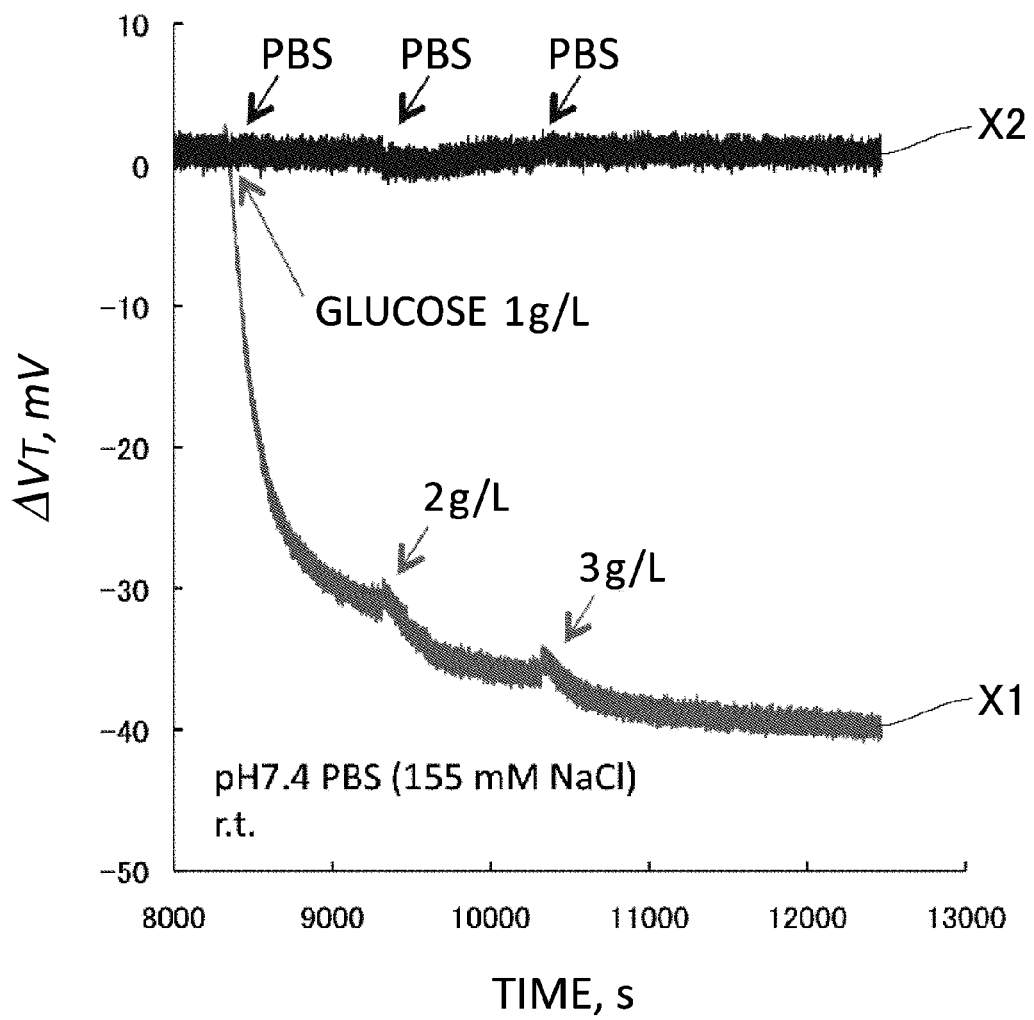
FIG. 4 is a graph that shows the relationship between glucose concentration and potential change.

The measurement result x1 shown in FIG. 4 ensured that the potential change becomes greater as the glucose concentration becomes higher in the biosensor that uses the phenylboronic acid compound 21 of the present invention. Thus, it could be ensured that in the biosensor the potential change becomes greater as the blood glucose level becomes higher from the glucose concentration of 1 g/L, which is a normal blood glucose level, to the glucose concentration of 2 g/L or 3 g/L, and therefore the biosensor can be applied for sensing a blood glucose level of a living body. It should be noted that x2 in FIG. 4 shows a measurement result that was obtained when no glucose was added to the sample solution that was retained within the sensing region of the biosensor, thereby ensuring that there was no potential change in the biosensor in this case.

Also, this measurement result ensured that with the phenylboronic acid compound 21 according to the present invention, measurement of a blood glucose level is possible even if the sample solution is under neutral pH condition. Further, it could be ensured that with the phenylboronic acid compound 21 according to the present invention, pKa can be set lower than 7.4, which is the level of a living body, and pKa decreases in a higher extent as the glucose concentration becomes higher.

(2) Second Embodiment

Figure 5:
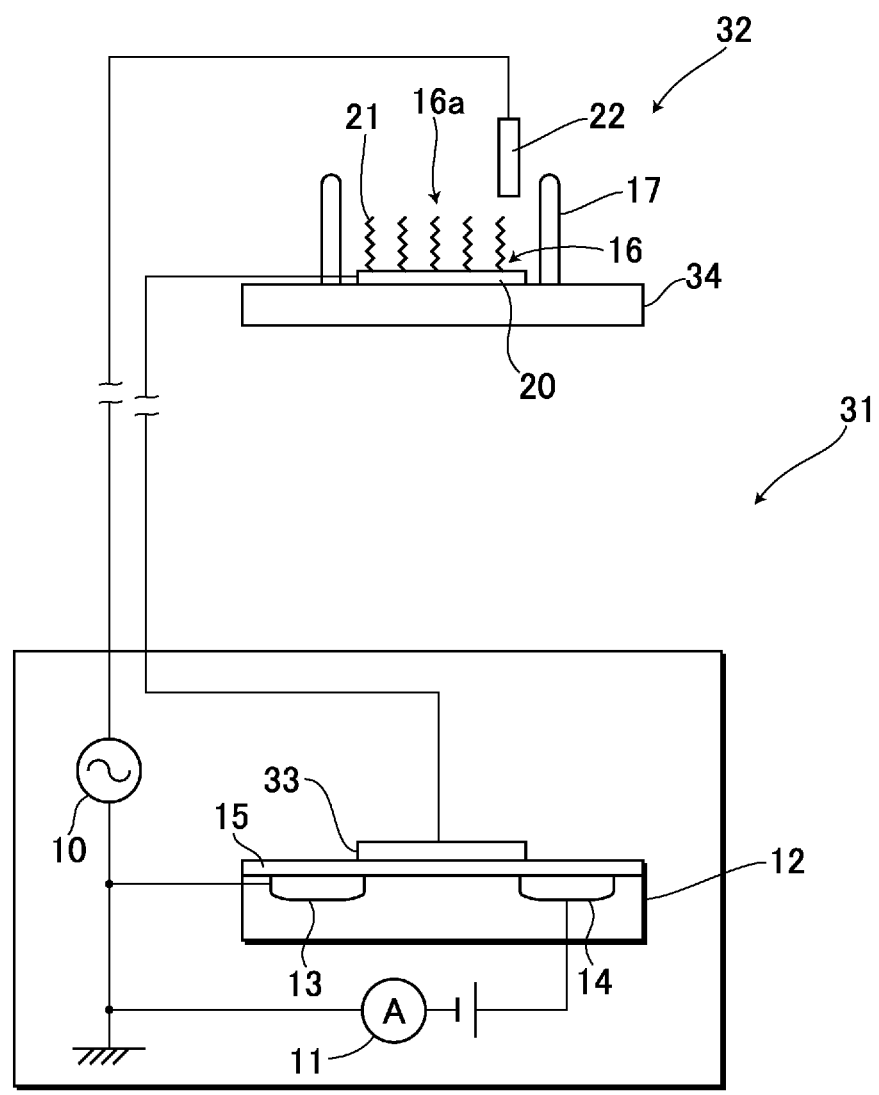
FIG. 5 is a schematic diagram that shows the configuration of the biosensor part according to the second embodiment.

In FIG. 5 in which a part corresponding to that in FIG. 1 is shown at the same reference numeral, 31 indicates a biosensor part according to the second embodiment, which is different in that the metal layer 20 of the sensing device 16 that was shown in the above-described first embodiment is separated from the gate insulating film 15. In this case, the biosensor part 31 has a structure in which the biosensor 32 that has a field effect transistor structure is divided into two.

Actually, in this biosensor 32, a gate-insulating-film-side metal layer 33 provided on the semiconductor substrate 12 via the gate insulating film 15 and a supporting substrate 34 on which the metal layer 20 is provided are separately configured, and the gate-insulating-film-side metal layer 33 and the metal layer 20 are connected via wiring.

Moreover, in the biosensor 32, the end of the phenylboronic acid compound 21 is chemisorbed to the substrate surface of the metal layer 20. When glucose in a glucose sample solution covalently binds to the phenylboronic acid compound 21 at the sensing surface 16a, a negative charge is generated. In response to this, the voltage applied to the metal layer 20 changes, and the current that flows between the source 13 and the drain 14 also changes. Thus, even the biosensor 32 with such as the structure can provide effects similar to those of the above-described first embodiment.

(3) Third Embodiment

Figure 6:
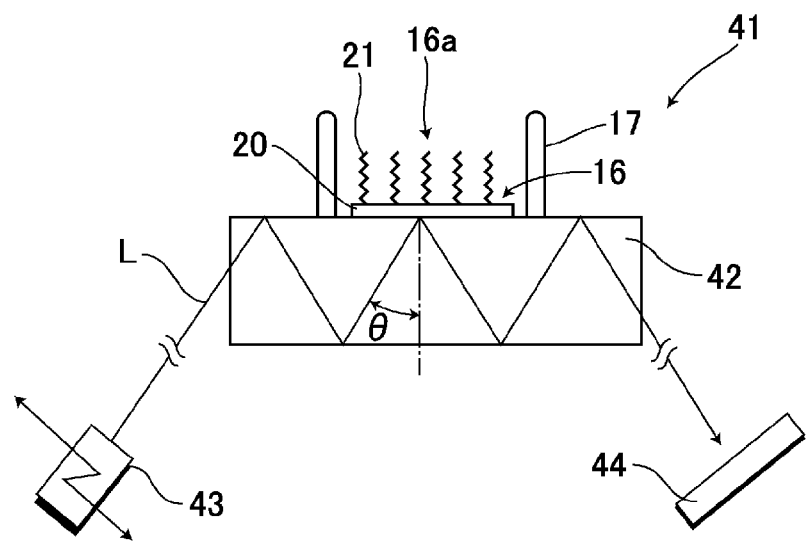
FIG. 6 is a schematic diagram that shows the overall configuration of the sensing system according to the third embodiment.

In FIG. 6 in which a part corresponding to that in FIG. 1 is shown at the same reference numeral, 41 indicates a biosensor according to the third embodiment, which has a structure that uses Surface Plasmon Resonance (SPR). Here, the SPR is for having a laser beam L to enter from one end surface of the solid-phase substrate 42, which is a sensing medium, to the metal layer 20 at an angle equal to or greater than the critical angle and thus generating surface plasmon at the boundary surface between the metal layer 20 and a sample that coats the substrate surface of the metal layer 20.

In this example, the metal layer 20 provided on the solid-phase substrate 42 is coated with the phenylboronic acid compound 21, and the laser beam L enters from the one end surface of the solid-phase substrate 42 at an angle equal to or greater than the critical angle by measurement light irradiation means 43. Here, the biosensor 41 is configured in such a manner that when glucose covalently binds to the phenylboronic acid compound 21, an attenuation change of the light intensity of the laser beam L occurs at the coated surface of the solid-phase substrate 42 that is coated with the metal layer 20.

The biosensor 41 can detect a change in the reflected light intensity that occurs at the coated surface (sensing surface) of the solid-phase substrate 42 with reflected light measuring means 44, acquire a refractive index at the coated surface from the attenuation of the light intensity, and, based on this refractive index, determine an amount of glucose in an examined sample.

Additionally, in a case where SPR is used as the biosensor 41 according to the present invention, optical systems that use an optical fiber, prism, diffraction grating, optical waveguide, or the like, can be employed as a method of inducing surface plasmon resonance; and glass, polymer resin, plastic, or the like, can be employed as an optical waveguide member of the solid-phase substrate 42 in the biosensor 41. The object to be measured in the surface plasmon resonance may be a wavelength of light, and may be an incident or reflection angle. An LED, LD, white light, or the like, can be used as a light source of the measurement light irradiation means 43, and a CCD, PD, optical position sensor, or the like, can be used as the reflected light measuring means 44.

(4) Fourth Embodiment

Figure 7:
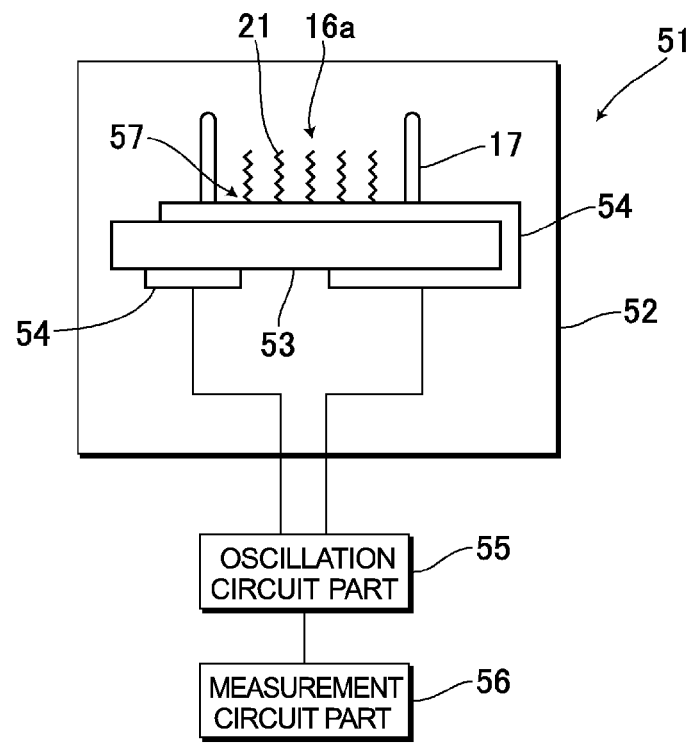
FIG. 7 is a schematic diagram that shows the overall configuration of the sensing system according to the fourth embodiment.

In FIG. 7 in which a part corresponding to that in FIG. 1 is shown at the same reference numeral, 51 indicates a biosensor according to the fourth embodiment, which has a structure that uses a Quartz Crystal Microbalance (QCM) sensor 52. Here, the QCM sensor 52 is a small and highly-sensitive mass detector that is capable of measuring the mass of trace substance adsorbed or bound to the surface of a quartz crystal oscillator 53 from a change in the resonance frequency of the quartz crystal oscillator 53.

In the biosensor 51 that uses the QCM sensor 52, the quartz crystal oscillator 53, which is a sensing medium, includes a piezoelectric member, an electrode 54 the substrate surface of which is coated with the phenylboronic acid compound 21 is formed at the surface of the quartz crystal oscillator 53, and the electrode 54 coated with the phenylboronic acid compound 21 is disposed so as to be in contact with a glucose sample (solution or gas). Then, the biosensor 51 obtains a change in mass characteristics that occurs due to the binding between the phenylboronic acid compound 21 and glucose in the electrode 54, as a change in oscillation characteristics such as an oscillation frequency with an oscillation circuit part 55, for example, and measures this with a measurement circuit part 56.

Additionally, in a case where the QCM sensor 52 is used for sensing glucose, a sensing device 57 that uses as a solid phase a matter in which the phenylboronic acid compound 21 to be bound to glucose is formed on the electrode 54 of the quartz crystal oscillator 53 is desirable. The quartz crystal oscillator 53 is provided in a container that is filled with a buffer solution, followed by addition of a glucose sample. The glucose binds to the phenylboronic acid compound 21 formed at the solid phase on the electrode 54 of the quartz crystal oscillator 53 and functions as a mass load, to thereby lower the resonance frequency of the quartz crystal oscillator 53. Such as the QCM sensor 52 can obtain an amount of mass change directly from an amount of frequency change, and thus has an advantage of not requiring a calibration curve.

The invention claimed is:
1. A sensing device comprising:
a metal layer configured to chemisorb a phenylboronic acid compound which recognizes saccharides or hydroxyl group-containing polymers, wherein the phenylboronic acid compound is represented by Formula (1):

[Formula 1]

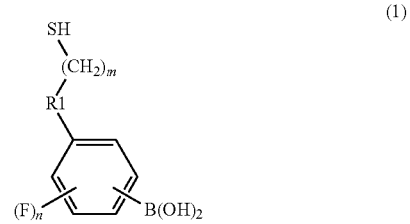

(where m is an integer equal to or greater than 1; F is independently present; n is any one of 1, 2, 3 and 4; and R1 represents a divalent linking group) and is chemisorbed to a substrate surface of the metal layer by a thiol group at an end.

2. The sensing device according to claim 1, wherein the Formula (1) is represented by Formula (2):

[Formula 2]

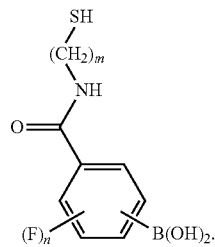

(2)

3. The sensing device according to claim 1, wherein the m is equal to or greater than 8.

4. A biosensor, wherein
the sensing device according to claim 1 is provided at a sensing medium, and
the sensing medium detects a change of any one or more physical characteristics among an optical characteristic, an oscillation characteristic and an electrical characteristic, the change occurring due to binding of a saccharide or hydroxyl group-containing polymer to the phenylboronic acid compound.

5. The biosensor according to claim 4, wherein
the sensing medium is a field effect transistor, and
the sensing device is provided on a gate insulating film of the field effect transistor.

6. The biosensor according to claim 5, wherein
the sensing device is disposed apart from the gate insulating film, and
a gate-insulating-film-side metal layer provided on the gate insulating film is electrically connected to the sensing device via wiring.

7. The biosensor according to claim 4, wherein
the sensing medium is an optical waveguide member in which the sensing device is provided at the external surface, and
an optical characteristic changes at a boundary portion between the optical waveguide member and the sensing device when the saccharide or hydroxyl group-containing polymer binds to the phenylboronic acid compound.

8. The biosensor according to claim 4, wherein
the sensing medium is a piezoelectric member in which the sensing device is provided at the external surface, and
an oscillation characteristic changes at a boundary portion between the piezoelectric member and the sensing device when the saccharide or hydroxyl group-containing polymer binds to the phenylboronic acid compound.

9. The sensing device according to claim 2, wherein the m is equal to or greater than 8.

10. A biosensor, wherein
the sensing device according to claim 2 is provided at a sensing medium, and
the sensing medium detects a change of any one or more physical characteristics among an optical characteristic, an oscillation characteristic and an electrical characteristic, the change occurring due to binding of a saccharide or hydroxyl group-containing polymer to the phenylboronic acid compound.

11. A biosensor, wherein
the sensing device according to claim 3 is provided at a sensing medium, and
the sensing medium detects a change of any one or more physical characteristics among an optical characteristic, an oscillation characteristic and an electrical characteristic, the change occurring due to binding of a saccharide or hydroxyl group-containing polymer to the phenylboronic acid compound.

* * * * *